US007993313B1

(12) United States Patent
Roche

(10) Patent No.: US 7,993,313 B1
(45) Date of Patent: Aug. 9, 2011

(54) APPARATUS AND METHOD FOR FACILITATING EMPTYING AN OSTOMY POUCH OR A PERSON'S BLADDER INTO A DISPOSABLE SEALABLE BAG

(76) Inventor: William P. Roche, Crystal River, FL (US)

( * ) Notice: Subject to any disclaimer, the term of this patent is extended or adjusted under 35 U.S.C. 154(b) by 0 days.

(21) Appl. No.: 12/586,333

(22) Filed: Sep. 21, 2009

(51) Int. Cl.
*A61F 5/44* (2006.01)
(52) U.S. Cl. ........ 604/345; 604/343; 604/349; 604/351; 604/353; 604/356; 604/334; 604/329
(58) Field of Classification Search .................. 604/345, 604/343, 349, 351, 353, 356, 329, 334
See application file for complete search history.

(56) References Cited

U.S. PATENT DOCUMENTS

| | | | |
|---|---|---|---|
| 718,794 A | 1/1903 | Reimard | |
| 1,634,532 A | 7/1927 | Bowe | |
| 2,228,360 A | 1/1941 | Nordeck | |
| 2,250,469 A | 7/1941 | Crow | |
| 2,494,632 A * | 1/1950 | Rodin | 248/102 |
| 2,584,249 A | 2/1952 | Belcher | |
| 3,906,957 A | 9/1975 | Weston | |
| 4,238,865 A | 12/1980 | Ingemann et al. | |
| 4,815,640 A * | 3/1989 | Johnson | 224/601 |
| 4,920,614 A | 5/1990 | Tsukamoto | |
| 5,349,724 A | 9/1994 | Barcina et al. | |
| 5,454,389 A * | 10/1995 | Hubbard et al. | 134/104.4 |
| 5,539,963 A | 7/1996 | Fujiwara et al. | |
| 5,569,225 A * | 10/1996 | Fleury | 604/323 |
| 5,647,670 A | 7/1997 | Iscovich | |
| 6,832,416 B2 | 12/2004 | Dixon | |
| 6,874,936 B2 | 4/2005 | Gillis et al. | |
| 7,682,347 B2 * | 3/2010 | Parks et al. | 604/355 |
| 2002/0148866 A1* | 10/2002 | Dent, III | 224/259 |
| 2003/0216702 A1* | 11/2003 | Butler | 604/332 |
| 2008/0294128 A1* | 11/2008 | Richards | 604/327 |

* cited by examiner

*Primary Examiner* — Tatyana Zalukaeva
*Assistant Examiner* — Ginger T Chapman
(74) *Attorney, Agent, or Firm* — Richard L. Miller, Registered Patent Agent

(57) ABSTRACT

An apparatus to receive feces from an ostomy pouch or urine from a person for disposal which comprises an adjustable strap member worn about a neck of the person to hang down therefrom. A waste receptacle is provided. A mechanism is for detachably mounting the waste receptacle to distal ends of the adjustable strap member at a groin area of the person. The person can discharge the feces from an open end of the ostomy pouch and also urinate into the waste receptacle.

6 Claims, 4 Drawing Sheets

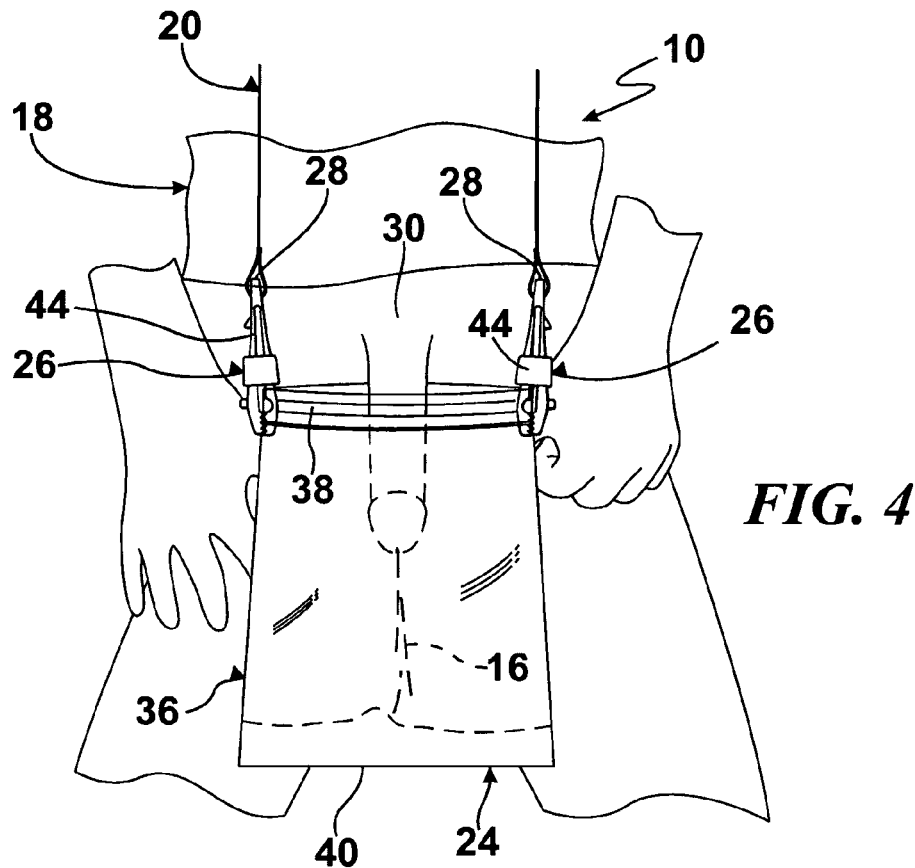
*FIG. 4*
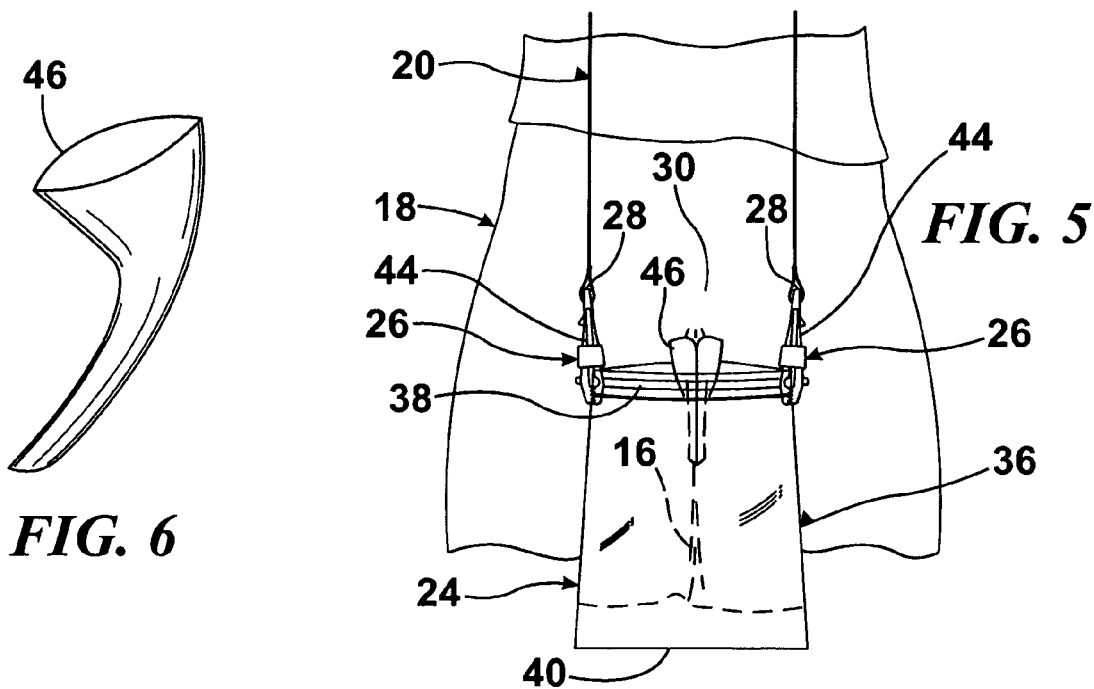
*FIG. 6*
*FIG. 5*

APPARATUS AND METHOD FOR FACILITATING EMPTYING AN OSTOMY POUCH OR A PERSON'S BLADDER INTO A DISPOSABLE SEALABLE BAG

BACKGROUND OF THE INVENTION

1. Field of the Invention

The present invention relates to a human waste collector, and more particularly, an apparatus and method for facilitating emptying an ostomy pouch or a person's bladder into a disposable sealable bag.

2. Description of the Prior Art

Numerous innovations for various apparatuses related to disposing of body waste fluids have been provided in the prior art that will be described. Even though these innovations may be suitable for the specific individual purposes to which they address, however, they differ from the present invention.

A FIRST EXAMPLE, U.S. Pat. No. 718,794, Issued on Jan. 20, 1903, to Reimard teaches a garment clasp comprising a pair of shanks continuous with a bend at one end and having jaws at their opposite ends, the shanks having outstruck ribs extending longitudinally thereof adjacent to their side edges and the one jaw formed with outstruck projections in longitudinal alignment between its ribs, and a slide movably engaging the jaws and having surrounding end beads, one of the latter at one side of the slide being struck inwardly to form a tongue to lock against the projections.

A SECOND EXAMPLE, U.S. Patent Office Document No. 1,634,532, Issued on Jul. 5, 1927, to Bowe teaches a clamp comprising a pair of pivotally connected jaws movable to and from clamping position, a member surrounding both jaws and movable thereon, one of the jaws having marginal portions angularly projecting from the jaw and the outer edges of the portion providing cam surfaces for engagement by the member whereby the jaws may be moved to clamping position.

A THIRD EXAMPLE, U.S. Patent Office Document No. 2,228,360, Issued on Jan. 14, 1941, to Nordeck teaches in a clothespin, a pair of independent complementary main parts; a V-shaped notch removed from but adjacent to the upper end of one main part; a V-shaped lug extending out from the other main part in complementary position to the V-shaped notch and loosely engaging therein to form a fulcrum about which the two parts may turn; the adjacent surfaces above and below the notch and lug of each of the two parts diverging at the notch and lug; an elastic cup fitting over the upper ends of the two parts above the fulcrum and tending to separate the lower ends thereof; a ring slidably mounted on the two parts and adapted to be forced downward thereon to clamp the lower ends thereof towards each other; and shoulders extending outward from points near the upper ends of each of the main parts and adapted to retain the clamping ring on the clothespin.

A FOURTH EXAMPLE, U.S. Patent Office Document No. 2,250,469, Issued on Jul. 29, 1941, to Crow teaches a clasp of the character described comprising a keeper having an upper and a lower arm spaced apart and connected at one end, the arms being substantially parallel and rigid, an upper and a lower gripping arm connected at one end by a spring eye, the eye and arms being slidably mounted between the arms of the keeper to assume either an inner closed position or an outer open position, and a hump-shaped surface formed on the upper gripping arm and engageable with one of the keeper arms to close the gripper arm with relation to the lower gripper arm.

A FIFTH EXAMPLE, U.S. Patent Office Document No. 2,584,249, Issued on Feb. 5, 1952, to Belcher teaches a colostomy device comprising a material receiving apron of funnel-like shape adapted to extend at the lower end into the bowl of a toilet, means adapted to detachably secure the apron at the front and top closely to the waist of a patient seated facing the toilet bowl, and means adapted to detachably secure the apron at the back to the toilet above the bowl; the last named means including a toe string.

A SIXTH EXAMPLE, U.S. Patent Office Document No. 3,906,957, Issued on Sep. 23, 1975, to Weston teaches forceps, either of the tweezer type or scissors-like type, in which cross-beaking of the jaws is resisted by the presence of a flexible connector attached between the forceps arms adjacent to the jaws. This connector is bowed away from the jaws and extends sufficiently in a plane at right angles to the plane of movement of the arms at the points of attachment to the arms to resist torsion during the operation of the forceps.

A SEVENTH EXAMPLE, U.S. Patent Office Document No. 4,238,865, Issued on Dec. 16, 1980, to Ingemann et al. teaches a boot support device that includes a pair of shanks which engage each other intermediate their ends but closest to the upper end of the device. The inter-engagement of the shanks effects a rocking movement between the shanks to cause the lower ends of the shanks to move apart to facilitate insertion into the legs of boots. The divergence of the lower ends is effected by causing sections of the shanks near the upper ends to be squeezed together. A predetermined divergence may be effected by movement into a certain position of a hollow slider which is displaceable along the shanks. Divergence of the lower ends of the shanks may also be effected by manually squeezing together opposed sides of a loop-shaped connection extending between the shanks at the upper end.

AN EIGHTH EXAMPLE, U.S. Patent Office Document No. 4,920,614, Issued on May 1, 1990, to Tsukamoto teaches a clamping device which has clamping units including a pair of openable arms extending in a V-shape toward one side of a pivotal center and in a X-shape toward both sides thereof, and a pair of retainers projecting from the ends of each of the arms a predetermined length toward the end, and a clamping means slidably engaged with parts of the arms of the clamping units for adjusting and holding the amount of closing of the arms in response to the thickness of an article to be clamped. The article is clamped and held by the force of restoration produced by the deformation of the clamping units occurring when the article is inserted between the pair of retainers and the pair of arms are closed.

A NINTH EXAMPLE, U.S. Patent Office Document No. 5,349,724, Issued on Sep. 27, 1994, to Barcina et al. teaches a device which forms the object of the present invention that comprises a flat element more than half of which is subdivided longitudinally into two parts. The external faces of the element are provided with longitudinal grooves and the internal faces are provided with longitudinal parallel ribs. The element is embraced by a bridge piece with laterally projecting wings and a number of inner ribs which slide within the grooves. To seal the opening of the container the lips of the opening are simply fitted between the two parts. Once in this position, the bridge piece is simply pushed along by pressing the projections with the fingers such that as it advances, guided by the coupling which exists between the ribs and the grooves, it applies pressure on the opening until it is perfectly sealed, the presence of the ribs eliminating any tendency of the new seal to slip.

A TENTH EXAMPLE, U.S. Patent Office Document No. 5,539,963, Issued on Jul. 30, 1996, to Fujiwara et al. teaches a clip body having upper and lower clamping pieces which flare continuously and from both ends of a bending portion in a desired width and a pressing cover having upper and lower clamping pieces continuously extending from both ends of a bending portion which is formed so as to provide a desired width, in which tops of the upper and lower clamping pieces are to be engaged with upper and lower parts close to the bending portion of the clip body, and a width formed between the tops being narrower than the maximum width formed between the upper and lower clamping portions of the clip body and wherein the pressing cover being slidably provided on the outer portions of the clip body so that both the upper and lower clamping pieces of the clip body approach each other in a pressing state.

AN ELEVENTH EXAMPLE, U.S. Patent Office Document No. 5,647,670, Issued on Jul. 1, 1997, to Iscovich teaches a containment system is described which is useful for the containment of bodily fluids, such as emesis or urine. The fluid containment system is a flexible polymeric bag, preferably polyethylene, of unitary construction having a closed end and a large, normally open, reinforced, "fish mouth" open end through which fluid is introduced into the bag, the reinforced open end having a press and seal closure mechanism. In one embodiment, a strap secures the bag, which is normally in the open or receiving position, around the neck of a person. In another embodiment, straps secure the bag to a belt or belt loops for the collection of urine. In operation, the bag is affixed to the body with a strap which is attached to the (normally open) end of the bag. If the bag is to be used for the collection of emesis, the strap is hung around the neck and dimensioned to position the bag below the chin. The open end of the bag is normally open to receive fluids. The user may, however, push together both ends of the reinforced open end of the bag to further enlarge the opening until the desired shape for the open end is reached. Once set, the open end of the bag will retain its shape. After the emesis occurs the bag can be removed and closed by peeling off a releasable protective strip to expose an inner adhesive strip and grasping the open end of the bag at both ends and pulling taut. The bag is then sealed by sliding the opposed thumb and forefinger along the outside of the bag adjacent to the adhesive strip to insure a liquid-tight seal closure. Self-sealing snaps at the top of the bag insure against accidental opening of the adhesive seal.

A TWELFTH EXAMPLE, U.S. Patent Office Document No. 6,832,416, Issued on Dec. 21, 2004, to Dixon teaches a clamp formed from a single block of resilient material, and preferably from nylon. A living hinge is formed that couples upper and lower jaws of the clamp. First and second arms extend rearwardly from the upper and lower jaws, respectively. A pivotally mounted camming member secured to one of the arms can be manually moved by a user from a first position, wherein it holds the jaws in tight, clamping engagement with an assembly position therebetween, to a second position in which the jaws can be opened. The clamp requires only a minimal degree of user effort during use, therefore making it particularly ideally suited for applications where a large plurality of the clamps must be used and repeatedly applied, then taken off from, one or more workpieces.

A THIRTEENTH EXAMPLE, U.S. Patent Office Document No. 6,874,936, Issued on Apr. 5, 2005, to Gillis et al. teaches a strap-on waste container for receiving thrown up stomach contents includes an elongated moisture proof bag having an open end, a rigid ring connected to the bag open end, and an elongated neck strap connected on one end to the ring. The neck strap allows for hands free use of the container so that the user or an assistant need not hold the container. The neck strap further includes a fabricated stress riser that causes the neck strap to break through the application of a threshold force, allowing for easy removal of the neck strap and container.

It is apparent now that numerous innovations for various apparatuses related to disposing of body waste fluids have been provided in the prior art that adequate for various purposes. Furthermore, even though these innovations may be suitable for the specific individual purposes to which they address, accordingly, they would not be suitable for the purposes of the present invention as heretofore described.

SUMMARY OF THE INVENTION

AN OBJECT of the present invention is to provide an apparatus and method for facilitating emptying an ostomy pouch or a person's bladder into a disposable sealable bag that avoids the disadvantages of the prior art.

ANOTHER OBJECT of the present invention is to provide an apparatus and method for facilitating emptying an ostomy pouch or a person's bladder into a disposable sealable bag that is simple and inexpensive to manufacture.

STILL ANOTHER OBJECT of the present invention is to provide an apparatus and method for facilitating emptying an ostomy pouch or a person's bladder into a disposable sealable bag that is simple to use.

BRIEFLY STATED, STILL YET ANOTHER OBJECT of the present invention is to provide an apparatus to receive feces from an ostomy pouch or urine from a person for disposal which comprises an adjustable strap member worn about a neck of the person to hang down therefrom. A waste receptacle is provided. A mechanism is for detachably mounting the waste receptacle to distal ends of the adjustable strap member at a groin area of the person. The person can discharge the feces from an open end of the ostomy pouch and also urinate into the waste receptacle. It allows a person to empty a pouch or bladder when no other facility and/or toilet is available.

The novel features which are considered characteristic of the present invention are set forth in the appended claims. The invention itself, however, both as to its construction and its method of operation, together with additional objects and advantages thereof, will be best understood from the following description of the specific embodiments when read and understood in connection with the accompanying drawing.

BRIEF DESCRIPTION OF THE DRAWING

The figures of the drawings are briefly described as follows:

FIG. 3 is a diagrammatic perspective view of the present invention per se, showing the clip members on the strap member ready to be connected to the disposable sealable bag;

FIG. 4 is a diagrammatic front view, with parts broken away, showing the present invention worn by a male person for collecting his urine in the disposable sealable bag;

FIG. 5 is a diagrammatic front view, with parts broken away, showing the present invention worn by a female person for collecting her urine in the disposable sealable bag;

FIG. 6 is a diagrammatic side perspective view showing the foldable disposable soft plastic funnel used by the female person in FIG. 5 in greater detail.

Figure 1:
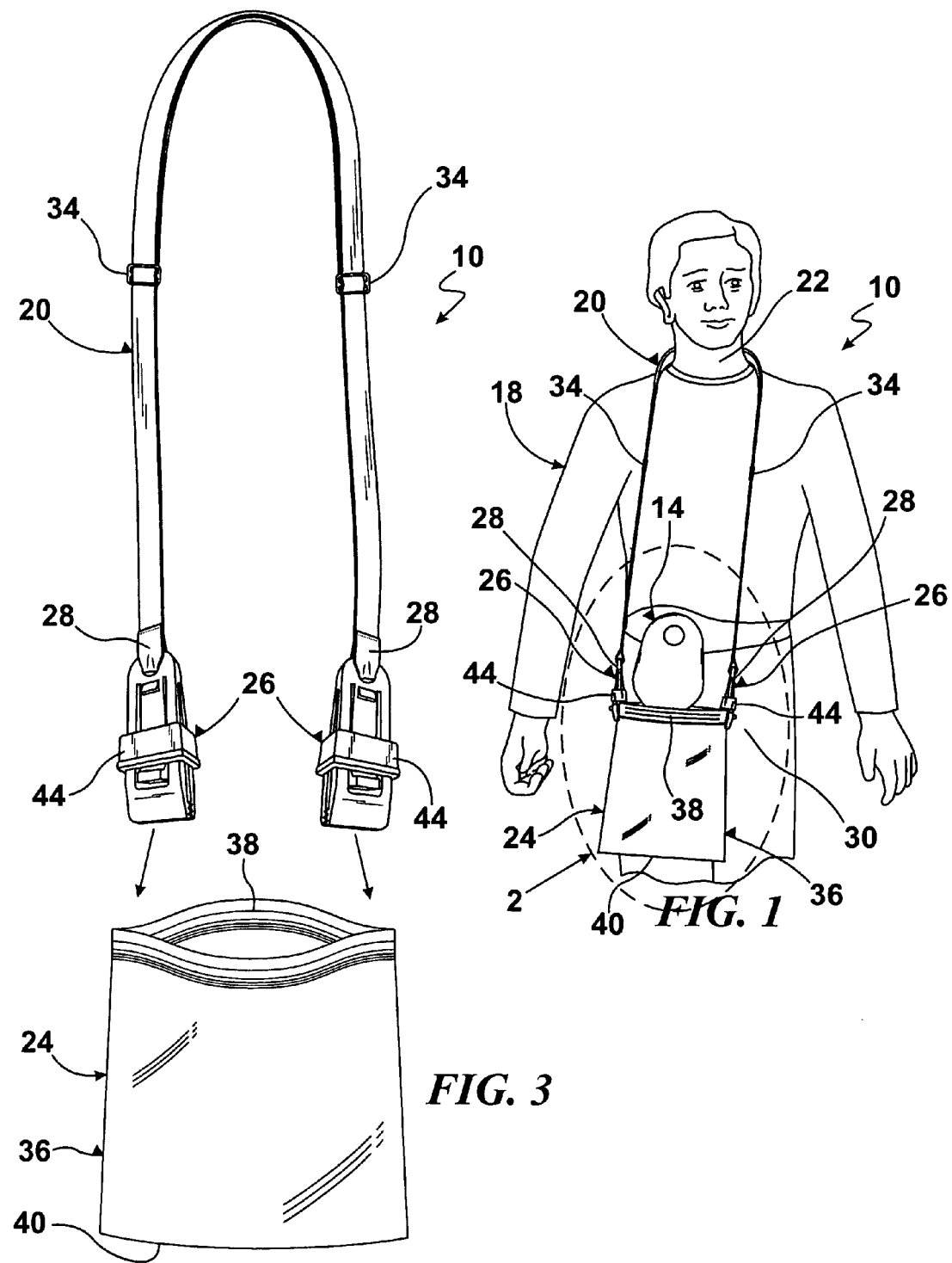
FIG. 1 is a diagrammatic front view showing an embodiment of the present invention worn by a person and being utilized to facilitate emptying an open ended ostomy pouch within a disposable sealable bag.
Figure 2:
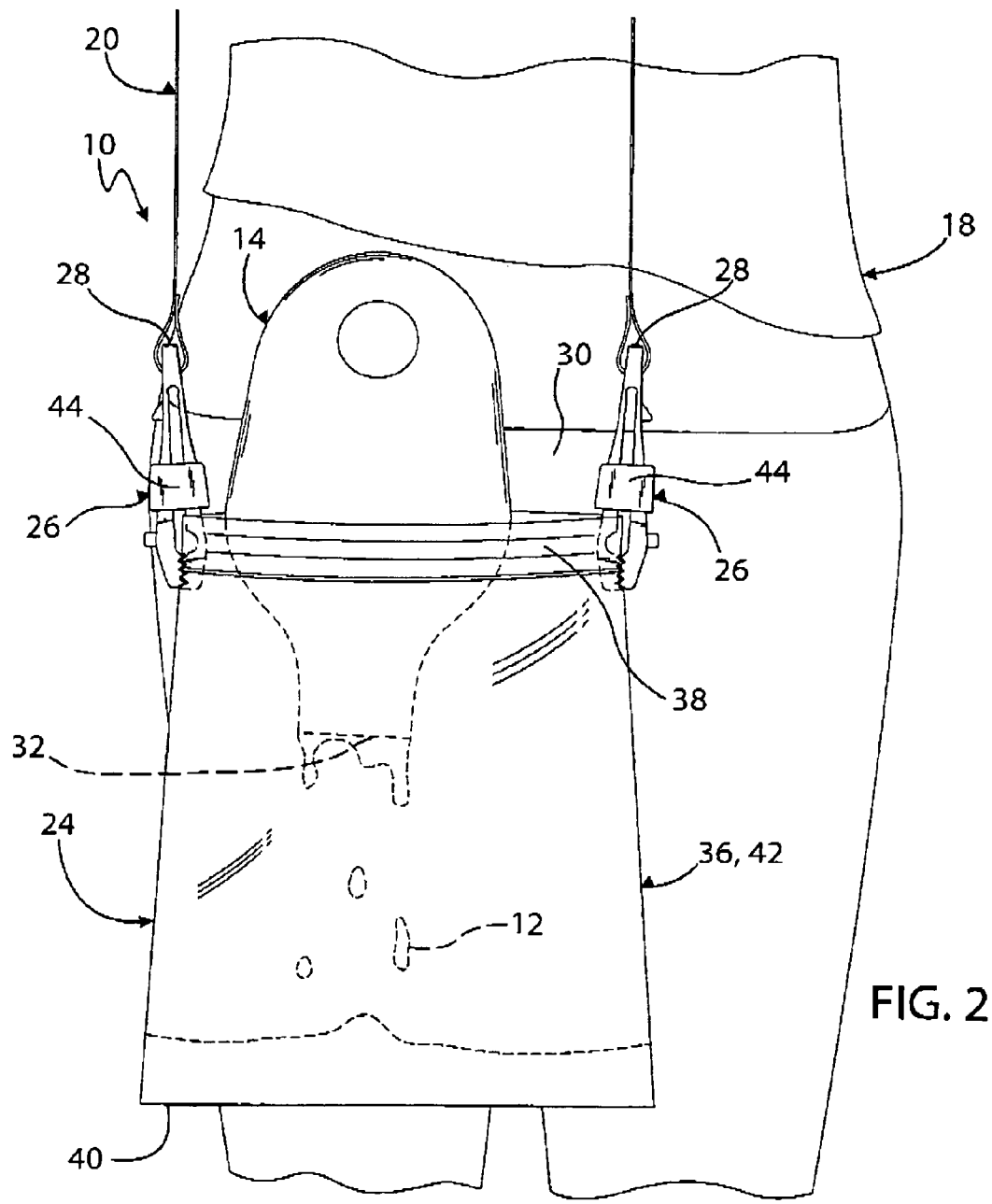
FIG. 2 is an enlarged diagrammatic front view of an area in the dotted circle as indicated by arrow 2 in FIG. 1.

A MARSHALING OF REFERENCE NUMERALS UTILIZED IN THE DRAWING 10 apparatus
12 feces
14 ostomy pouch
16 urine
18 person
20 adjustable strap member of apparatus 10
22 neck of person 18
24 waste receptacle of apparatus 10
26 detachably mounting mechanism of apparatus 10
28 distal end of adjustable strap member 20
30 groin area of person 18
32 open end of ostomy pouch 14
34 buckle on adjustable strap member 20
36 flexible disposable bag of waste receptacle 24
38 semi-rigid sealable mouth of flexible disposable bag 36
40 bottom end of flexible disposable bag 36
42 durable opaque vinyl material of flexible disposable bag 36
44 clip fastener of detachably mounting mechanism 26
46 foldable disposable soft plastic funnel of apparatus
48 carrying case of apparatus 10

DETAILED DESCRIPTION OF THE PREFERRED EMBODIMENT

Referring now to the figures, in which like numerals indicate like parts, and particularly to FIGS. 1 through 7, which are a diagrammatic front view showing an embodiment of the present invention worn by a person and being utilized to facilitate emptying an open ended ostomy pouch within a disposable sealable bag; an enlarged diagrammatic front view of an area in the dotted circle as indicated by arrow 2 in FIG. 1; a diagrammatic perspective view of the present invention per se, showing the clip members on the strap member ready to be connected to the disposable sealable bag; a diagrammatic front view, with parts broken away, showing the present invention worn by a male person for collecting his urine in the disposable sealable bag; a diagrammatic front view, with parts broken away, showing the present invention worn by a female person for collecting her urine in the disposable sealable bag; a diagrammatic side perspective view showing the foldable disposable soft plastic funnel used by the female person in FIG. 5 in greater detail; and a diagrammatic perspective view of a carrying case for storing the various components of the present invention therein, and as such, will be discussed with reference thereto.

The present invention is an apparatus 10 to receive feces 12 from an ostomy pouch 14 or urine 16 from a person 18 for disposal which comprises an adjustable strap member 20 worn about a neck 22 of the person 18 to hang down therefrom. A waste receptacle 24 is provided. A mechanism 26 is for detachably mounting the waste receptacle 24 to distal ends 28 of the adjustable strap member 20 at a groin area 30 of the person 18. The person 18 can discharge the feces 12 from an open end 32 of the ostomy pouch 14 and also urinate into the waste receptacle 24.

The adjustable strap member 20 comprises a pair of buckles 34 carried thereon, to adjust the length of the adjustable strap member 20 to properly reach the groin area 30 of the person 18. The waste receptacle 24 comprises a flexible disposable bag 36 having a semi-rigid sealable mouth 38 and closed bottom end 40. The flexible disposable bag 36 is comprised out of a durable opaque vinyl material 42.

The detachably mounting mechanism 26 comprises a pair of clip fasteners 44. Each clip fastener 44 is attached to a distal end 28 of the adjustable strap member 20 to engage with one outer edge of the semi-rigid sealable mouth 38 of the flexible disposable bag 36 to keep the semi-rigid sealable mouth 38 open to receive the feces 12 and urine 16 therein. The apparatus 10 further comprises a foldable disposable soft plastic funnel 46 to be used by a female person 18 to collect urine 16 into the waste receptacle 24 (See FIGS. 5 and 6).

Figure 7:
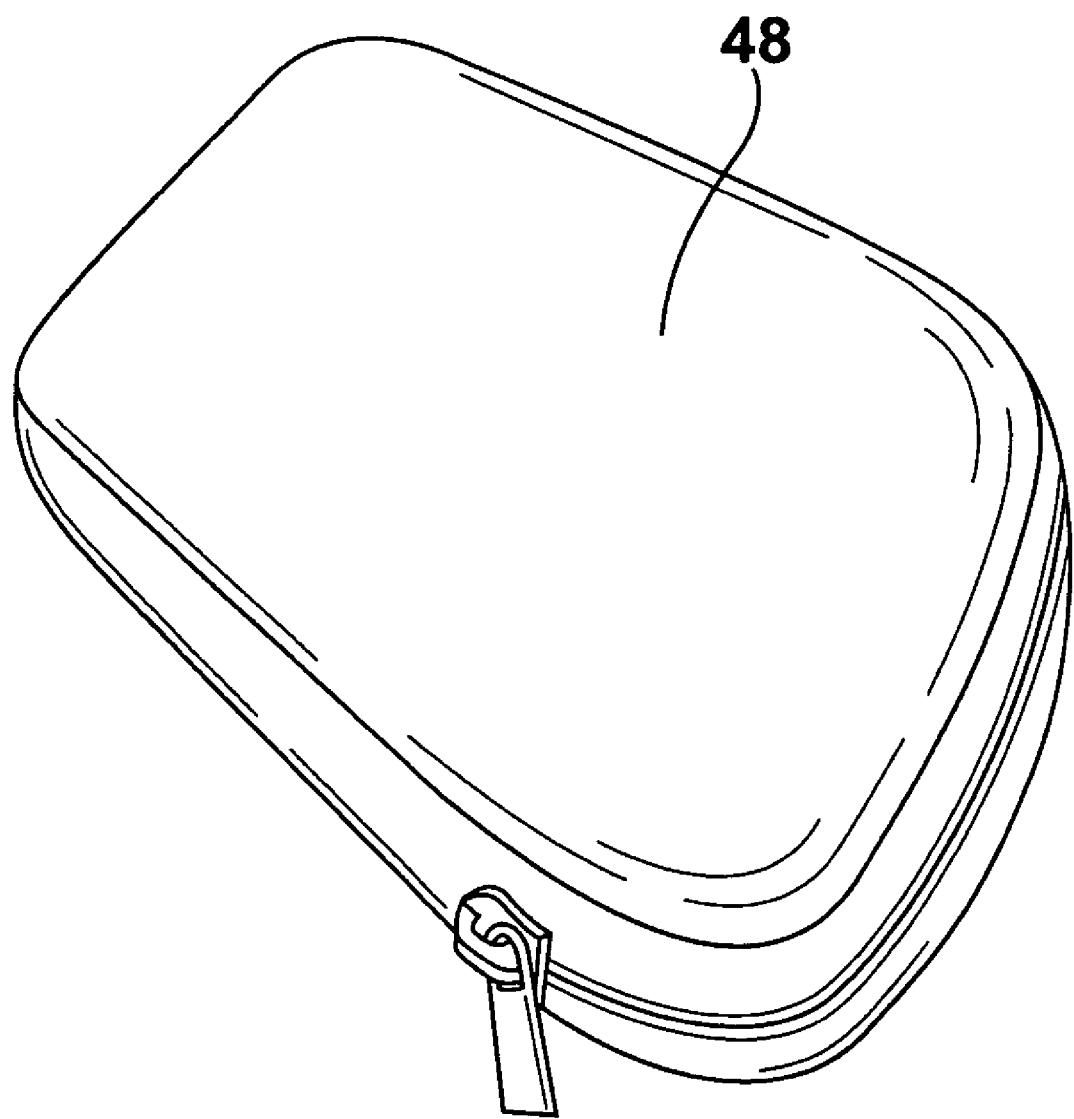
FIG. 7 is a diagrammatic perspective view of a carrying case for storing the various components of the present invention therein.

The apparatus 10 further comprises a carrying case 48 used to store the various components of the apparatus 10 therein when not in use (See FIG. 7).

To use the apparatus 10 the following steps should be taken:
1. Place the adjustable strap member 20 about the neck 22 of the person 18 to hang down therefrom.
2. Provide the waste receptacle 24.
3. Detachably mount the waste receptacle 24 to the distal ends 28 of the adjustable strap member 20 at the groin area 30 of the person 18, wherein the person 18 can discharge the feces 12 from the open end 32 of the ostomy pouch 14 and also urinate into the waste receptacle 24 for disposal.

It will be understood that each of the elements described above, or two or more together, may also find a useful application in other types of constructions differing from the types described above.

While the invention has been illustrated and described as embodiments of an apparatus and method for facilitating emptying an ostomy pouch or a person's bladder into a disposable sealable bag, accordingly it is not limited to the details shown, since it will be understood that various omissions, modifications, substitutions and changes in the forms and details of the device illustrated and its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute characteristics of the generic or specific aspects of this invention.

The invention claimed is:
1. An apparatus to receive feces from an ostomy pouch or urine from a person for disposal which comprises:
   a) an adjustable strap member worn about a neck of the person to hang down therefrom;
   b) a waste receptacle; and
   c) means for detachably mounting said waste receptacle to distal ends of said adjustable strap member at a groin area of the person, wherein the person can discharge the feces from an open end of the ostomy pouch and/or also urinate into said waste receptacle;
   wherein said waste receptacle comprises a flexible disposable bag having a semi-rigid sealable mouth and closed bottom end;
   wherein said detachably mounting means comprises a pair of clip fasteners; and
   wherein each said clip fastener is attached to a distal end of said adjustable strap member to engage with one outer edge of said semi-rigid sealable mouth of said flexible disposable bag to keep said semi-rigid sealable mouth open to receive the feces and urine therein.

2. The apparatus as recited in claim 1, wherein said adjustable strap member comprises a pair of buckles carried thereon, to adjust the length of said adjustable strap member to properly reach the groin area of the person.

3. The apparatus as recited in claim 1, wherein said flexible disposable bag is comprised out of a durable opaque material.

4. The apparatus as recited in claim 1, further comprising a foldable disposable soft plastic funnel to be used by a female person to collect urine into said waste receptacle.

5. The apparatus as recited in claim 4, further comprising a carrying case used to store the various components of said apparatus therein when not in use.

6. An apparatus to receive feces from an ostomy pouch or urine from a person for disposal which comprises:
   a) an adjustable strap member worn about a neck of the person to hang down therefrom;
   b) a waste receptacle; and
   c) means for detachably mounting said waste receptacle to distal ends of said adjustable strap member at a groin area of the person, wherein the person can discharge the feces from an open end of the ostomy pouch and/or also urinate into said waste receptacle;

wherein said adjustable strap member comprises a pair of buckles carried thereon, to adjust the length of said adjustable strap member to properly reach the groin area of the person;

wherein said waste receptacle comprises a flexible disposable bag having a semi-rigid sealable mouth and closed bottom end wherein said flexible disposable bag is comprised out of a durable opaque material;

wherein said detachably mounting means comprises a pair of clip fasteners, wherein each said clip fastener is attached to a distal end of said adjustable strap member to engage with one outer edge of said semi-rigid sealable mouth of said flexible disposable bag to keep said semi-rigid sealable mouth open to receive the feces and urine therein;

wherein a foldable disposable soft plastic funnel is used by a female person to collect urine into said waste receptacle; and wherein a carrying case is used to store the various components of said apparatus therein when not in use.

\* \* \* \* \*